US00PP36581P2

(12) United States Plant Patent
Carr

(10) Patent No.: US PP36,581 P2
(45) Date of Patent: Apr. 1, 2025

(54) ***ERYSIMUM* PLANT NAMED 'Cdcery3'**

(50) Latin Name: ***Erysimum* hybrid**
Varietal Denomination: Cdcery3

(71) Applicant: Charles Carr, Winchester (GB)

(72) Inventor: Charles Carr, Winchester (GB)

( * ) Notice: Subject to any disclaimer, the term of this patent is extended or adjusted under 35 U.S.C. 154(b) by 0 days.

(21) Appl. No.: 18/900,593

(22) Filed: Sep. 27, 2024

(30) Foreign Application Priority Data

Mar. 13, 2024 (QZ) ..... PBR 20240654

(51) Int. Cl.
*A01H 5/02* (2018.01)
*A01H 6/20* (2018.01)

(52) U.S. Cl.
USPC ..... Plt./263.1
CPC ..... *A01H 6/20* (2018.05)

(58) Field of Classification Search
USPC ..... Plt./263.1
CPC ..... A01H 6/20; A01H 5/02
See application file for complete search history.

*Primary Examiner* — Keith O. Robinson
(74) *Attorney, Agent, or Firm* — Penny J. Aguirre

(57) ABSTRACT

A new cultivar of *Erysimum* plant named 'Cdcery3' that is characterized by its early flowering from spring into summer in The United Kingdom, its flowers that are vibrant purple in color with minimal fading, its flowers and leaves that are large in size, its strong and upright stems, its low maintenance, well-branched, and compact plant habit, and its drought resistance and good winter hardiness in The United Kingdom.

3 Drawing Sheets

Botanical classification: *Erysimum* hybrid.
Variety denomination: 'Cdcery3'.

BACKGROUND OF THE INVENTION

The present invention relates to a new and distinct cultivar of *Erysimum* of hybrid origin that is botanically known as *Erysimum* 'Cdcery3'. 'Cdcery3' is a new cultivar of wallflower grown for use as an ornamental landscape plant.

The new cultivar derived from a controlled breeding program by the Inventor in Winchester, The United Kingdom. The goals of the breeding program are to create new cultivars of *Erysimum* that perform well in the garden, have large flowers with unique colors that do not fade easily, compact and well-branched plant habits, and dark green foliage.

The Inventor made crosses between 2011 and 2016 between unnamed and unpatented plants of *Erysimum* in the Inventor's breeding program as both the female and male parents. The seeds were pooled from the crosses and therefore the exact parents are unknown. 'Cdcery3' was selected as a single unique plant in 2018 from the resulting seedlings of the above crosses.

Asexual propagation of the new cultivar was first accomplished by stem cuttings in Winchester, The United Kingdom in 2017 by the Inventor in order to evaluate multiple plants. Asexual propagation by stem cuttings has determined that the characteristics of the new cultivar are stable and are reproduced true to type in successive generations.

SUMMARY OF THE INVENTION

The following traits have been repeatedly observed and are determined to be the characteristics of the new cultivar. These attributes in combination distinguish 'Cdcery3' as a unique cultivar of *Erysimum*.

1. 'Cdcery3' exhibits foliage that is silverly dark green in color.
2. 'Cdcery3' exhibits early flowering from spring into summer in The United Kingdom.
3. 'Cdcery3' exhibits flowers that are vibrant purple in color with minimal fading.
4. 'Cdcery3' exhibits flowers and leaves that are large in size.
5. 'Cdcery3' exhibits strong and upright stems.
6. 'Cdcery3' exhibits a low maintenance, well-branched, and compact plant habit.
7. 'Cdcery3' exhibits drought resistance and good winter hardiness in The United Kingdom.

'Cdcery3' can be most closely compared to the *Erysimum* cultivars 'Cdcery1', 'Cdcery2', and 'Bowles's Mauve' (not patented). 'Cdcery1' and 'Cdcery2' are both similar to 'Cdcery3' in having silvery dark green foliage, vibrant flowers with minimal fading, a low maintenance, well-branched, and compact plant habit, drought resistance and good winter hardiness. 'Cdcery1' differs from 'Cdcery3' in having flowers that are vivid red in color. 'Cdcery2' differs from 'Cdcery3' in having flowers that are warm orange in color. 'Bowles's Mauve' differs from 'Cdcery3' in having smaller flowers that are lighter purple in color that fades quickly and leaves that are smaller in size.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosures include but may not be limited to website listings by Plantipp, Kernock Park Plants, YouTube, Plantago, Globe Planter, and August 2024 Seeds Gazette.

BRIEF DESCRIPTION OF THE DRAWINGS

The accompanying color photographs illustrate the overall appearance and distinct characteristics of the new *Erysimum*. The photographs were taken of a 6-month-old plant of the new cultivar as grown in a greenhouse in 26-cm containers in Waddinxveen, The Netherlands.

The photograph in FIG. 1 provides a side view of 'Cdcery3' in bloom.

Figure 1:
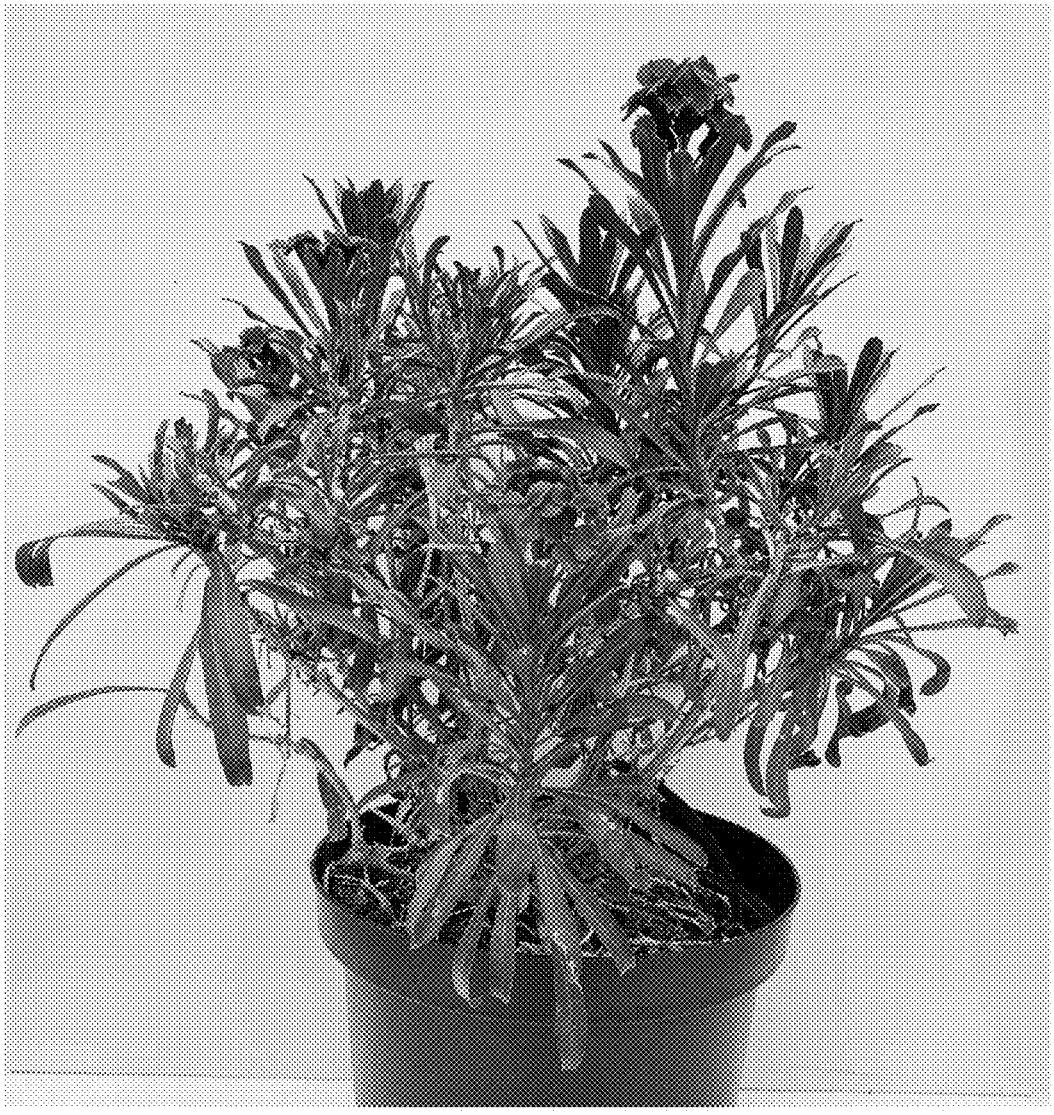
Figure 2:
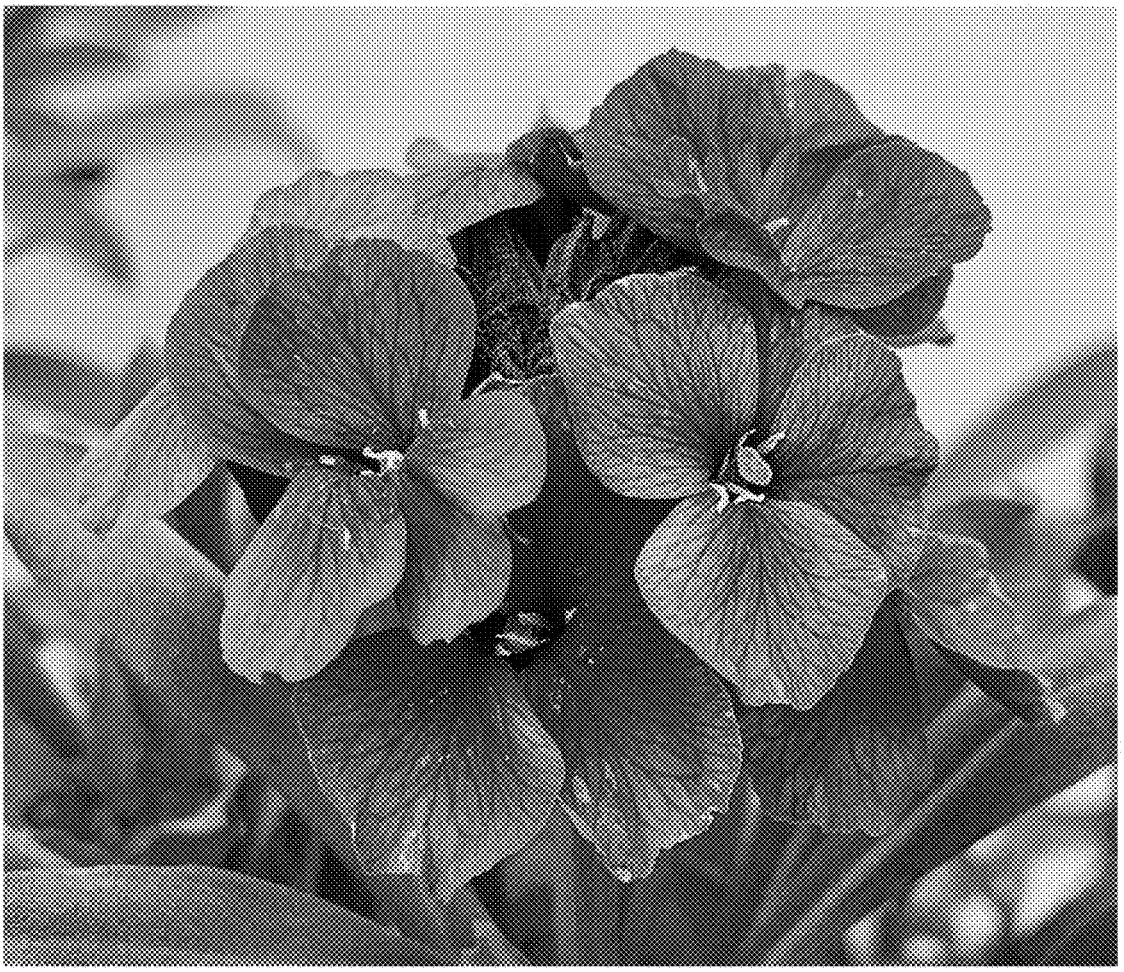

The photograph in FIG. 2 provides a close-up view of an inflorescence of 'Cdcery3'.

Figure 3:
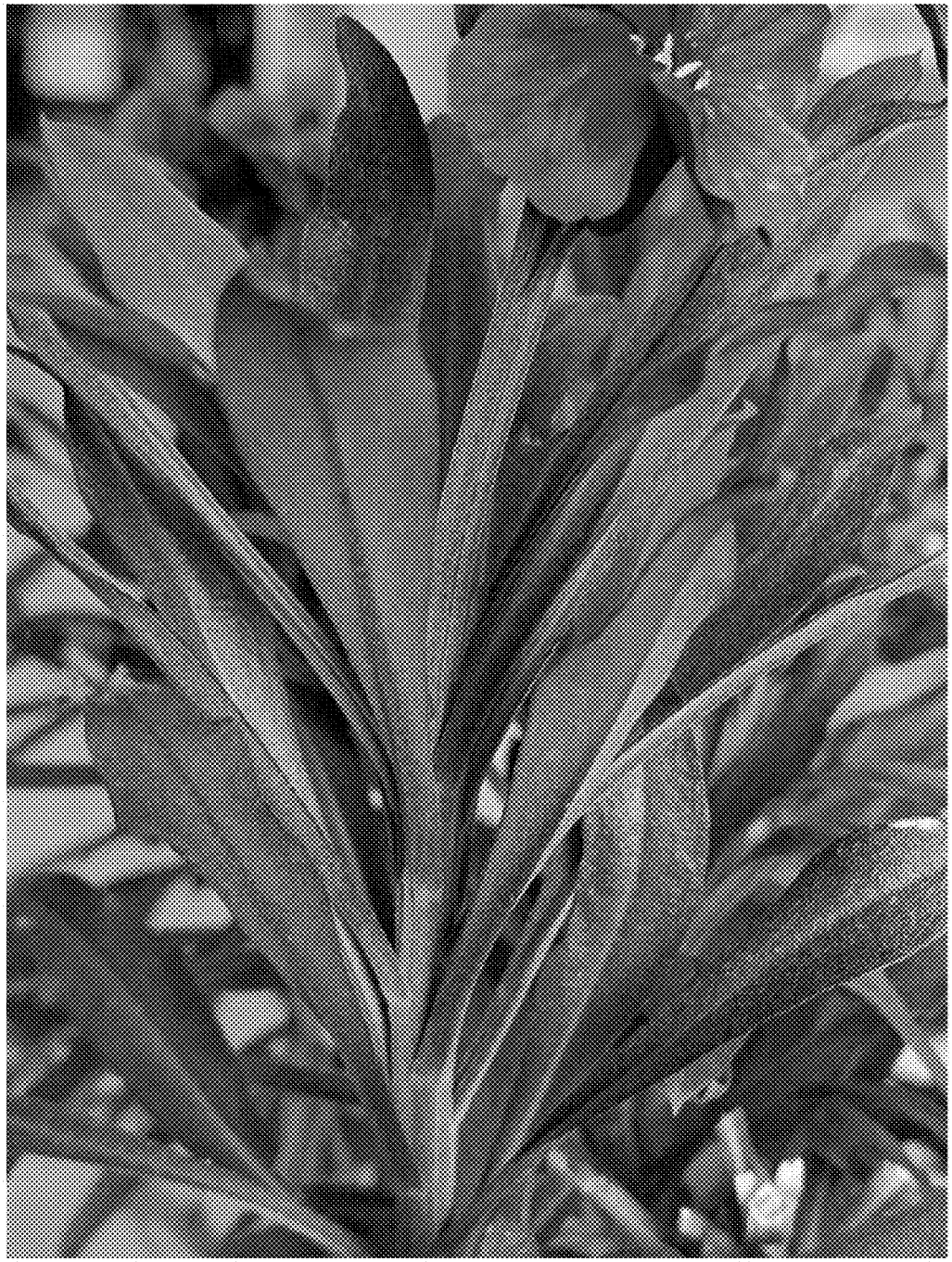

The photograph in FIG. 3 provides a close-up view of the foliage of 'Cdcery3'.

The colors in the photographs are as close as possible with the digital photography and printing techniques utilized and the color codes in the detailed botanical description accurately describe the new *Erysimum*.

DETAILED BOTANICAL DESCRIPTION

The following is a detailed description of 6-month-old plants of the new cultivar as grown in a greenhouse in 26-cm containers in Waddinxveen, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—March to July in The United Kingdom.

*Plant type*.—Herbaceous perennial.

*Plant habit*.—Compact, upright and mounded with upright stems.

*Height and spread*.—34 cm in height and 38 cm in spread as grown in a container, average of 50 cm in height and width as grown in the landscape.

*Hardiness*.—At least in U.S.D.A. Zone 6 to 9.

*Diseases and pests*.—No susceptibility or resistance to diseases or pests has been observed.

*Root description*.—Fine, fibrous.

*Propagation*.—Stem cuttings.

*Root development*.—6 to 7 weeks for root initiation, 10 to 12 weeks from a rooted cutting to young plant in a P17 container.

*Growth habit*.—Moderate.

Stem description:

*Stem size*.—Average of 22 cm in length (to base of peduncle) and 7 mm in diameter.

*Stem shape*.—Round.

*Stem color*.—144A, older wood; 199C.

*Stem surface*.—Slightly pubescent.

*Stem aspect*.—Held nearly upright.

*Internode length*.—1.5 cm.

*Branching habit*.—Freely branched, an average of 8 lateral stems off one main stem.

Foliage description:

*Leaf shape*.—Narrowly oblanceolate.

*Leaf division*.—Simple.

*Leaf base*.—Attenuate.

*Leaf apex*.—Acute.

*Leaf venation*.—Pinnate, color: young; upper surface 137A, base N77A, lower surface 137C, base N77A, mature; upper surface 145C and N77A, lower surface 144A.

*Leaf margins*.—Entire.

*Leaf attachment*.—Sessile.

*Leaf arrangement*.—Alternate.

*Leaf surface*.—Densely pubescent.

*Leaf color*.—Young; upper surface 137A, N77A base, lower surface 137C margins 137A, base N77A, mature; upper surface 137A and N77A, lower surface 137C and N77A.

*Leaf size*.—11.5 cm in length and 1.2 cm in width.

*Leaf quantity*.—An average of 24 per stem.

Flower description:

*Inflorescence type*.—Terminal raceme.

*Inflorescence quantity*.—Average of 10 per plant.

*Lastingness of inflorescence*.—Average of 7 days.

*Inflorescence size*.—An average of 2 cm in height and width.

*Flower fragrance*.—Light sweet fragrant.

*Flower number*.—Average of 8 open at one time.

*Flower aspect*.—Upright to outward, dependent on location of the inflorescence.

*Flower bud*.—An average of 8 mm in length and 4 mm in width, ovoid in shape, color; N79C, flushed with N77A towards the top.

*Flower type*.—Single.

*Flower size*.—Average of 2.5 cm in depth and diameter.

*Calyx*.—Tubular in form, an average of 1 cm in length and 8 mm in diameter.

*Sepals*.—4, lanceolate in shape, average of 1 cm in length and 2 mm in width, base truncate, entire margins, surfaces are glabrous, color; inner surface 137C, flushed 77A, outer surface N79A, base N77A.

*Petals*.—4, broadly obovate in shape, obtuse apex, attenuate base, entire margins, an average of 1 cm in length and 1.2 cm in width, color; young upper and lower surface 185B, mature upper surface center 77A, margins N81B, mature lower surface N81B.

*Peduncles*.—Round in shape, strong, an average of 6.5 cm in length and 4 mm in width, pubescent surface, color; 137A, flushed with N77A.

*Pedicels*.—Round in shape, strong, an average of 1 cm in length and 1 mm in width, densely pubescent surface, color; 137A, flushed with N77A.

Reproductive organs:

*Gynoecium*.—Pistil; 1, 9 mm in length, stigmas; 1 mm in length, round in shape, 145B in color, style; 6 mm in length, 145C in color, ovary; 144A in color.

*Androecium*.—Stamens; 6, anthers; oblong, 3 mm in length, 4D in color, filaments; adnate to corolla, 6 mm in length, color; 145B, older filaments N79C, pollen; moderate, 4D in color.

*Seeds*.—Not observed to date.

It is claimed:

1. A new and distinct cultivar of *Erysimum* plant named 'Cdcery3' as herein illustrated and described.

* * * * *